US012611394B2

(12) United States Patent (10) Patent No.: US 12,611,394 B2
Jing et al. (45) Date of Patent: Apr. 28, 2026

(54) USE OF GINKGOLIDE A IN THE TREATMENT OF AUTISM

(71) Applicants: CENTER FOR EXCELLENCE IN MOLECULAR CELL SCIENCE, CHINESE ACADEMY OF SCIENCES, Shanghai (CN); GUANGZHOU UNIVERSITY, Guangdong (CN)

(72) Inventors: Naihe Jing, Shanghai (CN); Ke Zhang, Shanghai (CN); Ke Tang, Guangdong (CN)

(73) Assignees: CENTER FOR EXCELLENCE IN MOLECULAR CELL SCIENCE, CHINESE ACADEMY OF SCIENCES, Shanghai (CN); GUANGZHOU UNIVERSITY, Guangzhou (CN)

( * ) Notice: Subject to any disclaimer, the term of this patent is extended or adjusted under 35 U.S.C. 154(b) by 955 days.

(21) Appl. No.: 17/773,213

(22) PCT Filed: Sep. 24, 2020

(86) PCT No.: PCT/CN2020/117543
§ 371 (c)(1),
(2) Date: Apr. 29, 2022

(87) PCT Pub. No.: WO2021/082826
PCT Pub. Date: May 6, 2021

(65) Prior Publication Data
US 2022/0409574 A1 Dec. 29, 2022

(30) Foreign Application Priority Data
Oct. 29, 2019 (CN) .......................... 201911039781.4

(51) Int. Cl.
*A61K 31/365* (2006.01)
*A61P 25/00* (2006.01)

(52) U.S. Cl.
CPC ............ *A61K 31/365* (2013.01); *A61P 25/00* (2018.01)

(58) Field of Classification Search
None
See application file for complete search history.

(56) References Cited

U.S. PATENT DOCUMENTS 6,187,314 B1 2/2001 Xie et al.
2001/0055629 A1 * 12/2001 Xie .......................... A61P 9/10
424/752

2010/0015259 A1 1/2010 Palmisano
2012/0157445 A1 6/2012 Garner et al.
2018/0104292 A1 * 4/2018 Lamensdorf ............ A61P 25/16

FOREIGN PATENT DOCUMENTS

CN 1159022 C 7/2004
CN 1837213 A * 9/2006
CN 100503613 C 6/2009

OTHER PUBLICATIONS

McKeage et al. (Drugs & Therapy Perspectives; 34:358-366, 2018).*
Bosch et al. (The American Journal of Human Genetics; 94, 303-309, Feb. 6, 2014).*
English translation of CN 1837213 (Sep. 27, 2006).*
Zhao, Jingyi, Non-official translation: "Formulation with Extracts from Ginkgo Biloba Leaves Using New Process Techniques," World Phytomedicines, vol. 15, No. 4, 2020, p. 174-178.
International Search Report mailed Dec. 1, 2020 in PCT/CN2020/117543 (w/ English translation).
First Chinese Office Action dated Sep. 23, 2021 issued in Chinese patent application No. 201911039781.4 (w/ English translation).
Hasanzadeh et al., "A Double-Blind Placebo Controlled Trial of *Ginkgo biloba* Added to Risperidone in Patients with Autistic Disorders," Child Psychiatry and Human Development, vol. 43, pp. 674-682, 2012.
Kuribara et al., "An Anxiolytic-Like Effect of *Ginkgo biloba* Extract and Its Constituent, Ginkgolide-A, in Mice," Journal of Natural Products, vol. 66, pp. 1333-1337, 2003.
Niederhofer, "First Preliminary Results of an Observation of *Ginkgo Biloba* treating Patients with Autistic Disorder," Phytotherapy Research, vol. 23, pp. 1645-1646, 2009.
Zhang et al., "Imbalance of Excitatory/Inhibitory Neuron Differentiation in Neurodevelopment Disorders with an NR2F1 Point Mutation," Cell Reports, vol. 31, pp. 1-18, 2020.
Extended European Search Report issued Sep. 25, 2023 in European Patent Application No. 20882980.4.

* cited by examiner

*Primary Examiner* — Bong-Sook Baek
(74) *Attorney, Agent, or Firm* — Banner & Witcoff, Ltd.

(57) ABSTRACT

Use of ginkgolide A in the treatment of autism. Specifically, the present invention relates to use of ginkgolide A, a stereoisomer thereof, a crystal form thereof, a pharmaceutically acceptable salt thereof, a derivative thereof, an extract comprising ginkgolide A, or a combination thereof in the preparation of a pharmaceutical composition for the treatment of autism. The experiments have demonstrated that ginkgolide A can significantly alleviate the behavioral defects of autism, and ginkgolide A has the advantages of small dosage and high safety when treating autism, and is very suitable as a common medicine for the treatment of autism.

8 Claims, 7 Drawing Sheets

|  | Number of wild type mice (+/+) | Number of heterozygous mutant mice (+/m) | Number of homozygous mutant mice (m/m) | Total numbers |
|---|---|---|---|---|
| Number | 26 | 45 | 0 | 71 |
| Ratio | 36.62% | 63.38% | 0% |  |
Figure    1
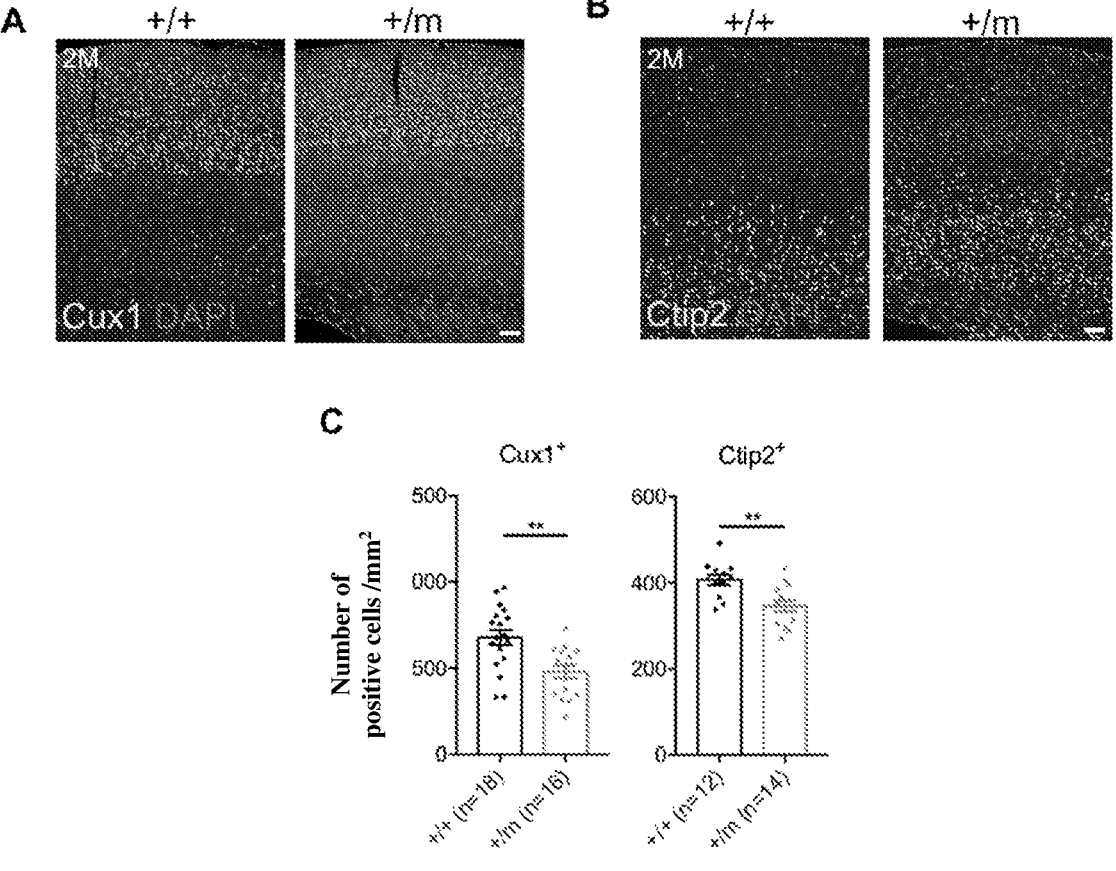
Figure    2

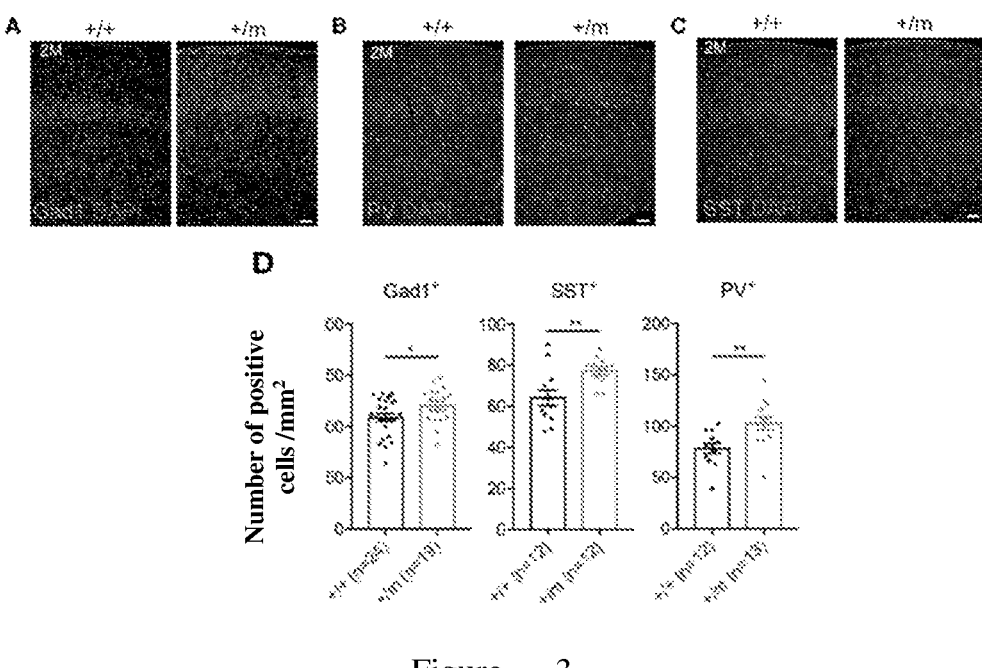
Figure     3
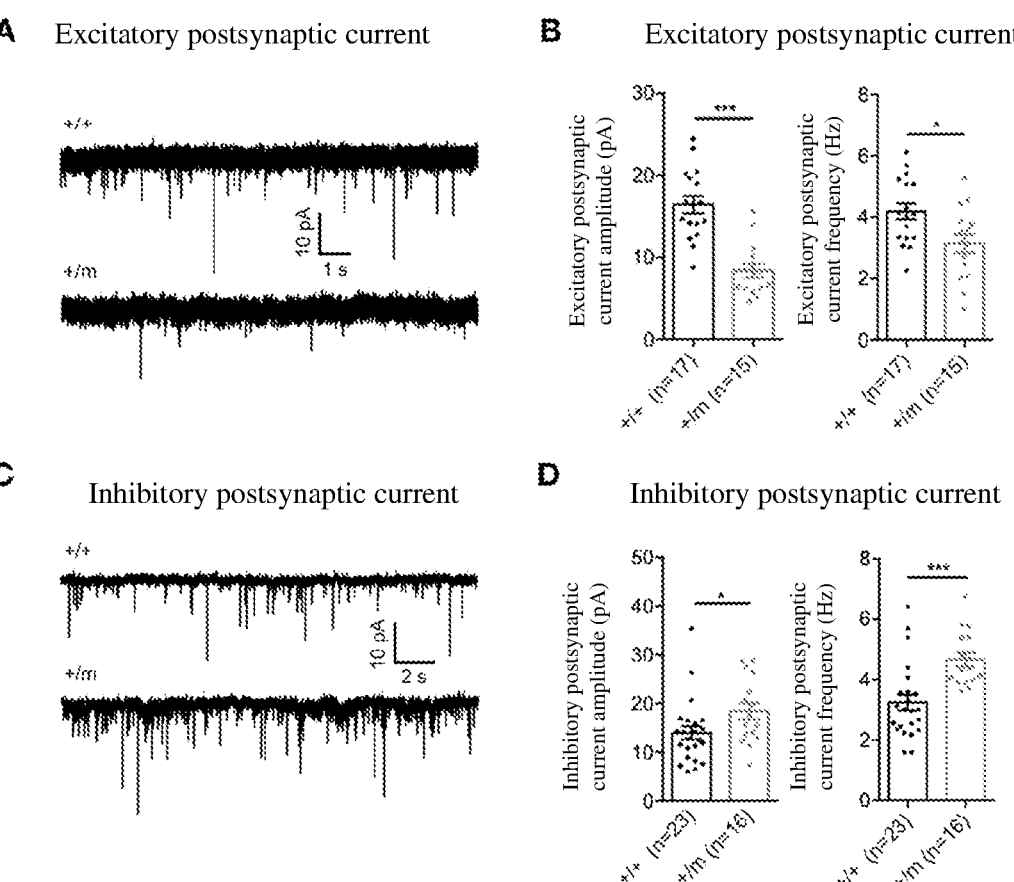
Figure     4

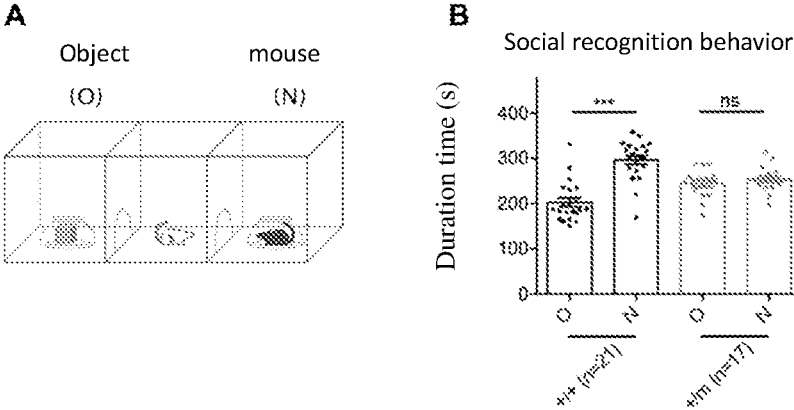
Figure    5
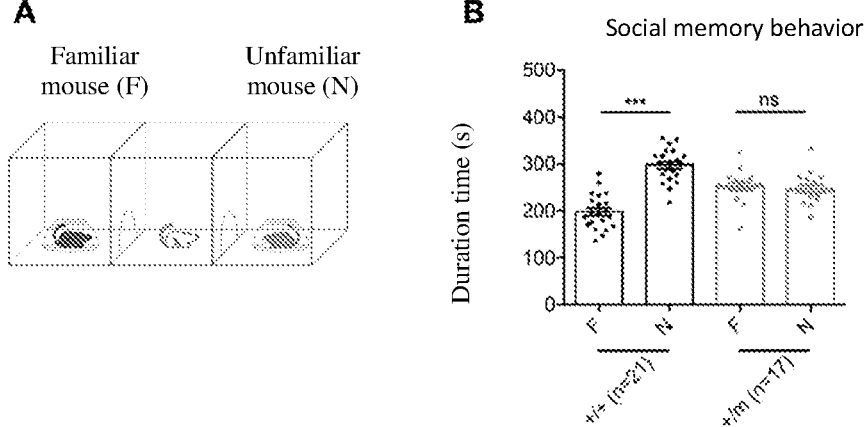
Figure    6

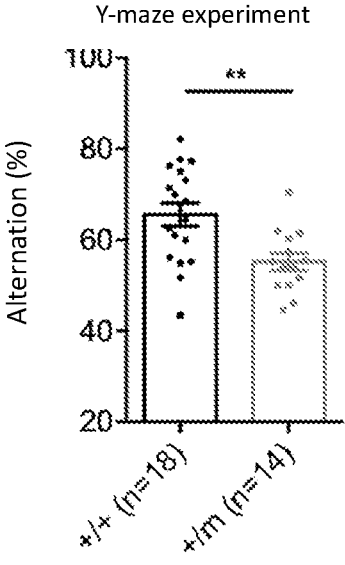
Figure    7
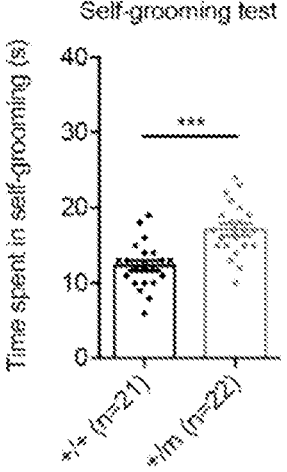
Figure    8

7 weeks
after birth 8 weeks
after birth 2 mg/kg ginkgolide A
oral gavage (every day)

Behavioral experiment

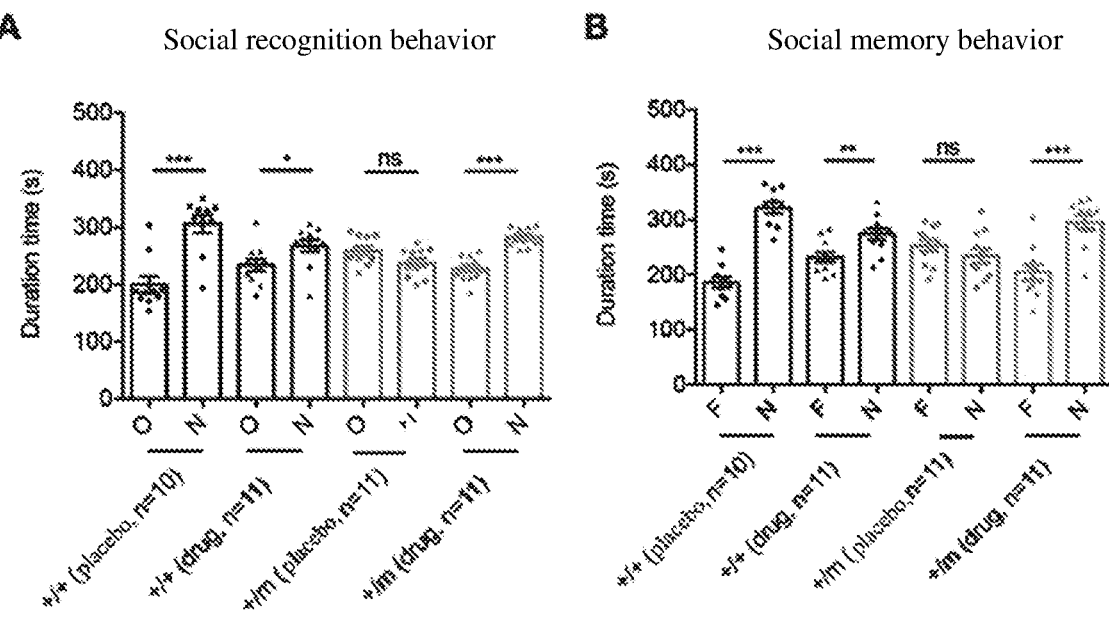
Figure    11
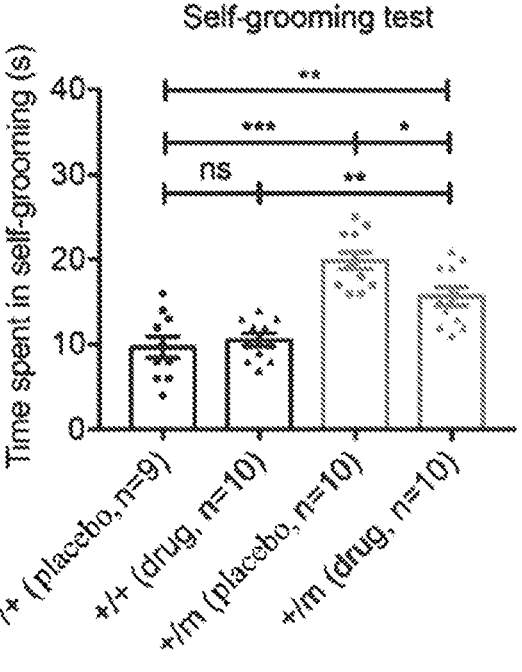
Figure    12

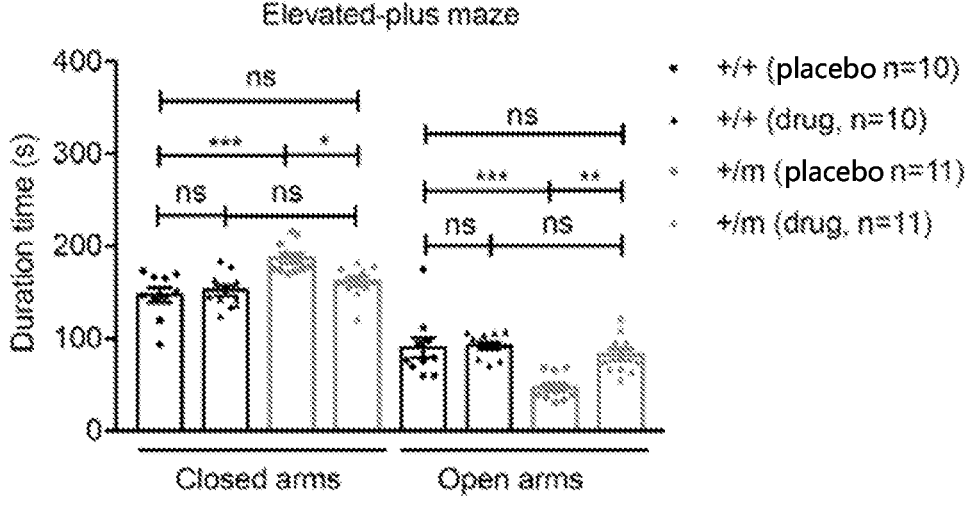
Figure    13

USE OF GINKGOLIDE A IN THE TREATMENT OF AUTISM

CROSS REFERENCE TO RELATED APPLICATIONS

This application is the National Stage of International Application No. PCT/CN2020/117543, filed Sep. 24, 2020, and claims benefit of Chinese Patent Application No. 201911039781.4 filed on Oct. 29, 2019, the full contents of all of which are hereby incorporated by reference in their entirety.

TECHNICAL FIELD

The invention relates to the field of medicine, specifically, the invention relates to the use of ginkgolide A in the treatment of autism spectrum disorder.

BACKGROUND

Autism spectrum disorder (Autism) is a kind of neurodevelopmental disorder syndrome, its symptoms include: social ability disorder, decreased verbal and non-verbal communication skill, narrow interest and repetitive stereotyped behavior. Professor Kanner in the United States observed the behavior of children with autism spectrum disorder in 1938 and officially reported it to the world for the first time in 1943.

Autism spectrum disorder is a neurodevelopmental disorder with complex phenotypes in infancy or childhood, and for now there is no effective treatment. Autistic patients often have great defects in feeling and behavior, but they are normal or even better in other aspects. For example, the IQ of 10% of autistic patient is significantly higher than that of the general population. There are great individual differences in the phenotype of autistic patient, which brings great difficulties to the diagnosis and identification of the disease. Autism spectrum disorder is often accompanied by a high degree of anxiety, for example, situations such as daily activities, environmental or character changes can make patients nervous, and often accompanied by self mutilation. Other common symptoms include abnormal eating, mental retardation, hyperactivity, distraction, lack of self-control, large emotional fluctuations. The symptoms of autistic patients appear very early. Generally, a clear phenotype can be observed within half a year of birth. The phenotype often lasts into adulthood and troubles the patient for life.

Therefore, there is an urgent need in this field to provide drugs that can effectively treat autism spectrum disorder.

SUMMARY OF THE INVENTION

The invention aims to provide use of ginkgolide A for the preparation of drugs for the treatment of autism spectrum disorder.

The first aspect of the present invention provides use of ginkgolide A, an stereoisomer thereof, a crystal form thereof, a pharmaceutically acceptable salt thereof, a derivative thereof, an extract containing ginkgolide A, and a combination thereof as a active ingredient for the preparation of a pharmaceutical composition for the treatment of autism spectrum disorder.

In another preferred example, the active ingredient is ginkgolide A, an stereoisomer thereof, a crystal form thereof, a pharmaceutically acceptable salt thereof, a derivative thereof, an extract containing ginkgolide A, and a combination thereof.

In another preferred example, the pharmaceutical composition further includes a pharmaceutically acceptable carrier.

In another preferred example, the active ingredient has a content of greater than 1 wt %, preferably, greater than 5 wt %, 10 wt %, 20 wt %, 30 wt %, 40 wt %, 50 wt %, 60 wt %, 70 wt %, 80 wt %, 90 wt %, 95 wt %, 98 wt %, 99 wt %, or 99.5 wt %, based on the total weight of the pharmaceutical composition.

In another preferred example, the extract containing ginkgolide A is *Ginkgo biloba* extract.

In another preferred example, in the extract containing ginkgolide A, the content of ginkgolide A C1 is greater than 5%, preferably, greater than 10%, more preferably, greater than 10 wt %, 20 wt %, 30 wt %, 40 wt %, 50 wt %, 60 wt %, 70 wt %, 80 wt %, 90 wt %, 95 wt %, 98 wt %, 99 wt %, or 99.5 wt %, based on the dry weight of the extract.

In another preferred example, the pharmaceutical composition is not used with other medications for the treatment of autism spectrum disorder.

In another preferred example, the dosage form of the pharmaceutical composition is selected from the group consisting of liquid preparation (e.g., solutions, emulsions, suspensions), and solid preparation (e.g., lyophilized formulations).

In another preferred example, the dosage form is selected from the group consisting of injection (e.g., injection liquid or powder injection), oral preparation (e.g., capsule, tablet, pill, powder, granule, syrup, oral liquid or tincture), and more preferably the dosage form is oral preparation.

In another preferred example, the treatment includes reducing the severity of autistic behavior defect and/or shortening the duration of autistic behavior defect.

In another preferred example, the autistic behavior defect is selected from the group consisting of social behavior disorder, decreased verbal communication skill, narrow interest, repetitive stereotyped behavior, anger, anxiety, and a combination thereof.

In another preferred example, the autism spectrum disorder is an autism caused by point mutation of Nr2f1 gene.

In another preferred example, the autism spectrum disorder is an autism caused by NR2F1-R112K point mutation.

In another preferred example, the autism spectrum disorder is an autism resulting from a decrease in the number of excitatory neurons and/or a decrease in nerve conduction activity and an increase in the number of inhibitory neurons and/or an increase in nerve conduction activity.

In another preferred example, the derivative is selected from the group consisting of 10-(2'-dimethylaminoethoxy)-ginkgolide A, 10-(2'-diethylaminoethoxy)-ginkgolide A, 10-((4'-methoxy-3', 5'-dimethyl-2'-pyridyl)-methoxy)-ginkgolide A, and 10-((2'-pyridyl)-ethoxy)-ginkgolide A.

The second aspect of the present invention provides a pharmaceutical composition for the treatment of autism behavior defect, comprising:

(a) an active ingredient: a therapeutically effective amount of ginkgolide A, an stereoisomer thereof, a crystal form thereof, a pharmaceutically acceptable salt thereof, a derivative thereof, an extract containing ginkgolide A, and a combination thereof; and (b) a pharmaceutically acceptable carrier.

In another preferred example, the active ingredient is ginkgolide A.

In another preferred example, the active ingredient has a content of greater than 1 wt %, preferably, greater than 5 wt %, 10 wt %, 20 wt %, 30 wt %, 40 wt %, 50 wt %, 60 wt %, 70 wt %, 80 wt %, 90 wt %, 95 wt %, 98 wt %, 99 wt %, or 99.5 wt %, based on the total weight of the pharmaceutical composition.

In another preferred example, the content of the active ingredient in the pharmaceutical composition is based on the weight of ginkgolide A.

In another preferred example, the extract containing ginkgolide A is *Ginkgo biloba* extract.

In another preferred example, in the extract containing ginkgolide A, the content of ginkgolide A C1 is greater than 5%, preferably, greater than 10%, more preferably, greater than 10 wt %, 20 wt %, 30 wt %, 40 wt %, 50 wt %, 60 wt %, 70 wt %, 80 wt %, 90 wt %, 95 wt %, 98 wt %, 99 wt %, or 99.5 wt %, based on the dry weight of the extract.

In another preferred example, the dosage form is selected from the group consisting of liquid formulations (e.g., solutions, emulsions, suspensions) and solid formulations (e.g., lyophilized formulations).

In another preferred example, the dosage form is selected from the group consisting of injection (e. g., injection liquid or powder injection), oral preparation (e. g., capsule, tablet, pill, powder, granule, syrup, oral liquid or tincture), and more preferably the dosage form is oral preparation.

In another preferred example, the pharmaceutical composition further comprises a therapeutic agent selected from the group consisting of antidepressant, antipsychotics, morphine blocker (e.g. Naltrexone), mood stabilizer (e.g. sodium valproate, carbamazepine, lithium carbonate, propranolol, clonazepam), central stimulant (e.g. methylphenidate (ritalin)), dopamine (DA) antagonist, antiepileptics, drugs for the treatment of tourette syndrome (e.g. Tiapride), haloperidol, inosine, Pimozide, vitamin B6, clonidine hydrochloride, and a combination thereof.

In another preferred example, the antidepressant is selected from the group consisting of tricyclic antidepressant (e.g., amitriptyline, imipramine, doxepin and clomipramine), tetracyclic antidepressant (e.g. maprotiline, amoxapine), selective serotonin reuptake inhibitor (e.g., fluoxetine, escitalopram, citalopram, sertraline, fluvoxamine), selective serotonin and norepinephrine reuptake inhibitor (e.g., venlafaxine, duloxetine, milnacipran), noradrenergic and specific serotonin antidepressant (e.g., mirtazapine), norepinephrine and dopamine reuptake inhibitor (e.g., bupropion), serotonin balanced antidepressant (e.g., trazodone), selective norepinephrine reuptake inhibitor (e.g., reboxetine), monoamine oxidase inhibitor (e.g., moclobemide), and combinations thereof.

In another preferred example, the antipsychotics is selected from the group consisting of chlorpromazine, sulpiride, haloperidol, risperidone, clozapine, olanzapine, and a combination thereof.

In another preferred example, the antiepileptics is selected from the group consisting of sodium valproate, topiramate, clonazepam, nitrodiazepam, and a combination thereof.

The third aspect of the present invention provides a method for treating autism spectrum disorder, comprising the step of:

administering a therapeutically effective amount of ginkgolide A, an stereoisomer thereof, a crystal form thereof, a pharmaceutically acceptable salt thereof, and a derivative thereof; an extract containing ginkgolide A, a combination thereof and the pharmaceutical composition described in the second aspect of the present invention to a subject in need thereof.

In another preferred example, the subject is mammal.

In another preferred example, the subject is human, rat or mouse.

In another preferred example, the subject carries a point mutation of NR2F1 gene.

In another preferred example, the subject carries NR2F1-R112K point mutation.

In another preferred example, the subject has an excitatory/inhibitory imbalance in the cerebral cortex, especially an increase in the inhibitory signal or/and a decrease in the excitatory signal.

It should be understood that within the scope of the present invention, the above-mentioned technical features of the present invention and the technical features specifically described in the following (such as examples) can be combined with each other to form a new or preferred technical solution. Due to space limitations, it will not be repeated one by one here.

DESCRIPTION OF THE DRAWINGS

FIG. 1 shows the statistical results of the number of mice with different genotypes.

FIG. 2-3 shows the results of immunostaining of mouse cerebral cortex at 2 months after birth.

FIG. 4 shows the schematic diagram (A) and statistical results (B) of micro excitatory potential synaptic current (mEPSC), and the schematic diagram (C) and statistical results (D) of micro inhibitory potential synaptic current (mIPSC).

FIG. 5 shows a schematic diagram (A) and statistical results (B) of the first round of the three-box experiment (sociability test) of wild-type (+/+) and heterozygous mutant (+/m) mice.

FIG. 6 is a schematic diagram (A) and statistical results (B) of the second round of the three-box experiment (social novelty test) of wild-type (+/+) and heterozygous mutant (+/m) mice.

FIG. 7 shows the statistical results of the Y-maze test of wild-type (+/+) and heterozygous mutant (+/m) mice, and the alternation % of mice continuously entering different experimental arms is counted to test their spatial memory ability.

FIG. 8 shows the statistical results of self-grooming test of wild-type (+/+) and heterozygous mutant (+/m) mice and the time of self-grooming behavior of wild-type and heterozygous mutant mice is counted.

FIG. 11 shows the behavioral statistical results of the three-box experiment (sociability and social novelty test) of wild-type (+/+) and heterozygous mutant (+/m) mice after administration, in which the placebo group is the vehicle group and the drug group is the ginkgolide A group.

FIG. 12 shows the behavioral statistical results of self-grooming test of wild-type (+/+) and heterozygous mutant (+/m) mice after administration, in which the placebo group is the vehicle group and the drug group is the ginkgolide A group.

FIG. 13 shows the behavioral statistical results of the elevated-plus maze experiment of wild-type (+/+) and heterozygous mutant (+/m) mice after administration, in which the placebo group is the vehicle group and the drug group is the ginkgolide A group.

Figure 9:
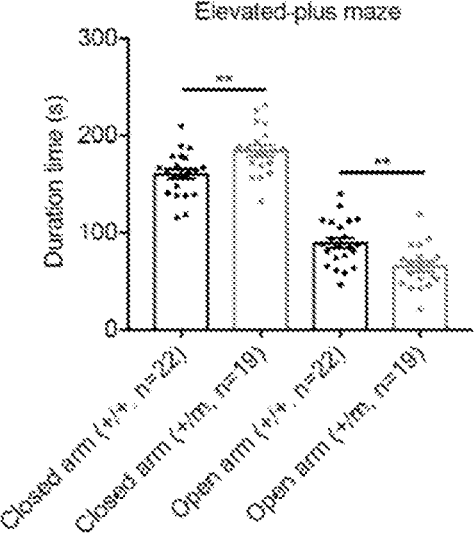
FIG. 9 shows the statistical results of elevated-plus maze experiment of wild-type (+/+) and heterozygous mutant (+/m) mice.

In each figure, +/+ refers to wild-type mice; +/m refers to heterozygous mutant mice.

DETAILED DESCRIPTION OF THE INVENTION

After extensive and intensive research and through a large number of screening and testing, the inventor provided the use of ginkgolide A for the preparation of drugs for the treatment of autism spectrum disorder. Experiments have proved that ginkgolide A can significantly alleviate the behavioral defects of autism spectrum disorder in mice, and can be used as drugs for the treatment of autism spectrum disorder, providing a new medication choice for the treatment of autism spectrum disorder. On this basis, the present invention is completed.

Definition

Unless specifically indicated otherwise, all technical and scientific terms used herein have the same meaning as commonly understood by those of ordinary skill in the art to which this invention belongs.

As used herein, the term "about" means that the value may change by no more than 1% from the enumerated value when referred to a specific enumerated value. For example, as used herein, the expression "about 100" includes all values between 99 and 101 (e. g., 99.1, 99.2, 99.3, 99.4, etc.).

As used herein, the terms "contain" or "include (comprise)" may be open, semi-closed, and closed. In other words, the term also includes "basically consisting of" or "consisting of".

The "treatment" of the present invention includes delaying and terminating the progression of the disease, or eliminating and regressing the disease. The regression of the disease is manifested by a decrease in the severity of the disease symptoms, an increase in the frequency and the duration of the asymptomatic period of the disease, or the prevention of the disorder or disability caused by the disease, and does not require 100% inhibition, elimination and reversal.

As used herein, the terms "heterozygous mutant mouse" and "mutant mouse" are used interchangeably to refer to heterozygous mutant model mouse carrying NR2F1 gene point mutation of the present invention.

Active Ingredient

The active ingredient of the invention is ginkgolide A, its stereoisomer, its crystal form, its pharmaceutically acceptable salt, its derivative, an extract containing ginkgolide A, or a combination thereof.

The structural formula of ginkgolide A is as follows:

As used herein, the term "stereoisomer" is intended to include all possible optical isomers, such as single chiral compounds, or mixtures of various chiral compounds (i.e., racemates). Among all the compounds of the present invention, each chiral carbon atom may optionally be in R configuration or S configuration, or mixtures thereof.

The inhibitors of the present invention may be used in the form of amorphous, crystalline or mixtures thereof.

As used herein, the term "pharmaceutically acceptable salt" refers to a salt formed by a compound of the present invention with an acid or base suitable to be used as drug. Pharmaceutically acceptable salts include inorganic and organic salts. A preferred class of salt is the salt formed by the compound of the present invention and acid. Acids suitable for salt formation include but are not limited to: inorganic acid such as toluene sulfonic acid, hydrochloric acid, hydrobromic acid, hydrofluoric acid, sulfuric acid, nitric acid, phosphoric acid and the like; organic acid such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenesulfonic acid and the like; and acidic amino acid such as aspartic acid, glutamic acid and the like. A preferred class of salt is the salt formed by the compound of the invention and a base. Bases suitable for salt formation include but are not limited to inorganic base such as sodium hydroxide, potassium hydroxide, sodium carbonate, sodium bicarbonate, sodium phosphate and the like; and organic base such as ammonia, triethylamine, diethylamine and the like.

In the present invention, the derivatives of ginkgolide A may be those disclosed in Chinese application CN100503613C, the entire contents of which are incorporated herein by reference.

Ginkgolide A can be extracted from *Ginkgo biloba* leaves. Typically, extraction methods include, but are not limited to, solvent extraction, column extraction, solvent extraction-column extraction, supercritical extraction, chromatography or column chromatography and the like.

In another preferred example, in the extract containing ginkgolide A, the content of ginkgolide A C1 is greater than 5%, preferably, greater than 10%, more preferably, greater than 10 wt %, 20 wt %, 30 wt %, 40 wt %, 50 wt %, 60 wt %, 70 wt %, 80 wt %, 90 wt %, 95 wt %, 98 wt %, 99 wt %, or 99.5 wt %, base on the dry weight of the extract.

Pharmaceutical Composition, Use

The pharmaceutical composition of the present invention comprises: (a) an active ingredient: a therapeutically effective amount of ginkgolide A, its stereoisomer, its crystal form, its pharmaceutically acceptable salt, its derivative, an extract containing ginkgolide A, or a combination thereof; and (b) a pharmaceutically acceptable carrier.

The pharmaceutical composition of the present invention can improve/alleviate autism spectrum disorder. In particular, it alleviates autistic behavior defects, which typically include (but are not limited to): social behavior disorder, decreased verbal communication skill, repeated stereotyped behavior, anger, anxiety, or a combination thereof.

As used herein, the term "therapeutically effective amount" refers to any amount of a drug described below that, when used alone or in combination with another therapeutic agent, can promote regression of the disease, which manifests itself as a decrease in the severity of the disease symptoms, an increase in the frequency and the duration of the asymptomatic period of the disease, or the prevention of the disorder or disability caused by the disease. The "therapeutic effective amount" of the drug of the invention also includes "preventive effective dose". The "preventive effective dose" is any amount of the drug as described below. When this amount of the drug is administered alone or in combination with another therapeutic agent to a subject at risk of developing the disease or suffering a recurrence of the disease, the occurrence or recurrence of the disease can be inhibited. Typically, the pharmaceutical composition contains 1-2000 mg of the compound of the present invention/dose, and more preferably 10-500 mg of the compound of the present invention/dose. Preferably, "a dose" is a capsule or tablet.

"Pharmaceutically acceptable carrier" refers to one or more compatible solid or liquid filler or gel substances that are suitable for human use and must have sufficient purity and sufficiently low toxicity. "Compatibility" herein means that each component of the composition can be mixed with the compound of the invention and between them without significantly reducing the efficacy of the compound. Examples of pharmaceutically acceptable carriers include cellulose and its derivatives (such as sodium carboxymethyl cellulose, sodium ethyl cellulose, cellulose acetate), gelatin, talc, solid lubricants (such as stearic acid, Magnesium stearate), calcium sulfate, vegetable oil (such as soybean oil, sesame oil, peanut oil, olive oil), polyols (such as propylene glycol, glycerin, mannitol, sorbitol), emulsifiers (such as Tween @), wetting agents (such as sodium dodecyl sulfate), colorants, flavoring agents, stabilizers, antioxidants, preservatives, pyrogen-free water.

There are no special restrictions on the administration of the compounds or pharmaceutical compositions of the invention. Representative methods of administration include (but are not limited to): oral, rectal, parenteral (intravenous, intramuscular or subcutaneous), and topical administration.

Solid dosage forms for oral administration include capsules, tablets, pills, powders and granules. In these solid dosage forms, the active compound is mixed with at least one conventional inert excipient (or carrier), such as sodium citrate or dicalcium phosphate, or with the following ingredients: (a) fillers or compatibilizers, such as starch, lactose, sucrose, glucose, mannitol and silicic acid; (b) adhesives, such as hydroxymethylcellulose, alginate, gelatin, polyvinylpyrrolidone, sucrose and Arabic gum; (c) humectants, e.g., glycerol; (d) disintegrants, e.g., agar, calcium carbonate, potato starch or tapioca starch, alginic acid, some composite silicates, and sodium carbonate; (e) slow solvents, e.g., paraffin; (f) absorption accelerators, e.g., quaternary amine compounds; (g) wetting agents, such as, talc, calcium stearate, magnesium stearate, solid polyethylene glycol, sodium dodecyl sulfate, or mixtures thereof. In capsules, tablets and pills, the dosage form may also contain buffers.

Solid dosage forms such as tablets, sugar pills, capsules, pills and granules can be prepared using coatings and shell materials, such as casings and other materials well known in the art. They may contain opaque agents, and the release of active compounds or compounds in this composition may be released in a part of the digestive tract in a delayed manner. Examples of embedding components that can be used are polymeric substances and waxes. If necessary, the active compound may also be in microencapsulated form with one or more of the excipients described above.

Liquid dosage forms for oral administration include pharmaceutically acceptable emulsions, solutions, suspensions, syrups or tinctures. In addition to the active compound, the liquid dosage form may include inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the composition may also include adjuvants such as wetting agents, emulsifiers and suspending agents, sweeteners, flavoring agents and spices.

In addition to the active compounds, the suspension may contain suspending agents, such as ethoxylated isooctadecanol, polyoxyethylene sorbitol and dehydrated sorbitol ester, microcrystalline cellulose, aluminum methoxide and agar or mixtures of these substances.

The composition for external parenteral injections may include sterilized aqueous or anhydrous solutions, dispersions, suspensions or emulsions that are physiologically acceptable, and a sterile powder for re-dissolution into a sterile injectable solution or dispersion. Suitable aqueous and non-aqueous carriers, diluents, solvents or excipients include water, ethanol, polyols and suitable mixtures thereof.

The dosage forms of the compound of the invention for topical administration include ointment, powder, patch, spray and inhalant. The active ingredient is mixed under sterile conditions with a physiologically acceptable carrier and any preservatives, buffers, or propellants that may be required if necessary.

The compound of the invention can be administered alone or in combination with other pharmaceutically acceptable compounds.

In some embodiments, the Hedgehog signaling pathway inhibitors of the present invention are used in the same or separate formulations simultaneously with, or sequentially with, other agents that are part of the combination therapy regimen.

The general range of therapeutically effective amount of a compound of Formula I or a composition of the compound of Formula I will be about 1-2000 mg/day, about 10-1000 mg/day, about 10-500 mg/day, about 10-250 mg/day, about 10-100 mg/day, or about 10-50 mg/day. The therapeutically effective amount will be given in one or more doses. It should be understood that the specific dose of the compound of the invention for any particular patient will depend on a variety of factors, such as the age, gender, weight, general health status, diet, individual response of the patient to be treated, time of administration, severity of the disease to be treated, activity of the specific compound administered, dosage form, mode of application and concomitant drugs. The effective amount of treatment in a given situation can be determined by routine experiments and within the ability and judgment of clinicians or doctors. In any case, the compound or composition will be administered in multiple doses based on the individual condition of the patient and in a manner that allows delivery of a therapeutically effective amount.

The main advantages of the present invention include:

1. Use of ginkgolide A in the treatment of autism spectrum disorder is disclosed in the present invention for the first time. The experiment shows that ginkgolide A can significantly improve the behavioral defects of autism spectrum disorder in mice and has excellent treatment effect on autism spectrum disorder.

2. Currently, there is no medicine for autism spectrum disorder. The invention provides a new drug choice for the treatment of autism spectrum disorder and is of great significance for the rapid and economical development of drugs for the treatment of autism spectrum disorder.

3. Ginkgolide A, as a known compound in the art, has high drug safety, and small side effects. The present invention found that the concentration of Ginkgolide A is as low as 2 mg/kg at a once-a-day administration frequency in the treatment of autism spectrum disorder in mice, indicating that ginkgolide A has a small effective drug dose and that Ginkgolide A is very suitable as a common drug for treating autism spectrum disorder.

The invention is further described below in combination with specific examples. It should be understood that these embodiments are only used to illustrate the invention and not to limit the scope of the invention. The experimental methods without specific conditions in the following embodiments are usually based on conventional conditions, such as Sambrook et al., molecular cloning: the conditions described in the laboratory manual (New York: Cold Spring Harbor Laboratory Press, 1989), or the conditions recommended by the manufacturer. Unless otherwise stated, percentages and portions are calculated by weight.

2. Experimental Materials and Methods 2.1 Experimental Materials 2.1.1 Mice

Wild type C57BL/6 mice were bred in the experimental animal center of Shanghai Institute of Biochemistry and cell biology, Chinese Academy of Sciences by two pairs of mice purchased from slaker experimental animal center. By the beginning of this experiment, wild-type and mutant mice had been bred and passaged on for more than 5 generations in the Experimental Animal Center of Shanghai Institute of Biochemistry and Cell Biology, Chinese Academy of Sciences. The feeding environment maintains a circadian rhythm of 12:12 h, the temperature is maintained at 20-24° C., and the air humidity is about 50-60%. The animals were kept in a $(28*12*16)$ cm$^3$ standard resin rat cage with shaving bedding, and were free to take in enough water and feed. Animal breeding and all experimental operations comply with the relevant regulations of the Experimental Animal Ethics Committee of the Shanghai Institute of Biochemistry and Cell Biology, Chinese Academy of Sciences.

2.1.2 Reagents

Pregnant mare serum gonadotropin (PMSG; Ningbo Sansheng Pharmaceutical);

Sodium chloride injection (Shandong Hualu Pharmaceutical Co., Ltd.);

Chorionic Gonadotropin for injection (HCG; Ningbo Sansheng Pharmaceutical);

Rabbit-derived polyclonal antibody:

Cux1 (1:25, Santa Cruz Inc.);

Ctip2 (1:200, Abcam);

PV (1:4000, Abcam);

SST (1:4000, a gift from Penisula lab);

Gad1 (1:200, Sigma);

Cy3-coupled goat anti mouse IgG (1:500, Jackson ImmunoResearch Laboratories);

Cy3-coupled goat anti rabbit IgG (1:500, Jackson ImmunoResearch Laboratories);

FITC-coupled goat anti mouse IgG (1:500, Jackson ImmunoResearch Laboratories);

FITC-coupled goat antirabbit IgG (1:500, Jackson ImmunoResearch Laboratories);

Other immune related reagents:

Paraformaldehyde (PFA stock solution: 10% in 1×PBS, final concentration: 4%); Normal goat serum (NGS, GIBCO); Normal mouse IgG (Santa Cruz); Normal rabbit IgG (Santa Cruz); DAPI (sigma, stock solution: 5 mg/ml, final concentration: 1 µg/ml-2 µg/ml, reusable); The sealing agent mowil was purchased from calbiochem; OCT frozen section embedding agent was purchased from Leica company. ProteinA, ProteinG PLUS Agarose (Santa Cruz); Dynabeads Protein A/G (Invitrogen); Protein A/G Agarose/Salmon Sperm DNA (Upstate).

Ginkgolide A is purchased from Selleck (https://www.selleck.cn/products/ginkgolide-a.html) with purity >99.5%.

Ginkgolide A 2.1.3 Instruments

Biorad PTC-100/S1000 PCR instrument, ABI 2720 PCR instrument, Eppendorf Realplex2 quantitative PCR instrument, Beckman DU650 ultraviolet spectrophotometer, Bio-Rad Pac 3000 electrophoresis instrument, UVP M26 ultraviolet glue illuminator, SONY DP71 thermal printer, Eppendorf 5417 refrigerated centrifuge, Thermo Picol7 room temperature centrifuge, Beckman Avanti J-E JSE 07B10 large refrigerated centrifuge, Beckman L-100K ultraspeed freezing centrifuge, BayGene small centrifuge, Mettler Toledo pH meter, Eppendorf MixMate oscillator, Thermo forma—80° C. refrigerator, cell incubator and ClassII biosafety cabinet, Su Jing Antai cell culture ultrastatic stage, Aria flow cytometer, Olympus BX51/IX71 fluorescence microscope, Olympus SZX10/16 Stereo microscope, BioRad Radiance 2100 inverted laser confocal microscope, Leica SP2 ortho laser confocal microscope, Turner Design 2020 Lumimetor, Leica CM1900 Cryostat Microtome, Samsung 16° C. constant temperature wine cabinet, bioRad Pac basic and Tanon EPS300 electrophoresis instrument, electrophoresis membrane transfer device, Shanghai Yiheng constant temperature biochemical incubator, Taicang Hualida HZ-9210K constant temperature shaker, DGX-9023 and 9140 blast dryer, WH-986 silent mixer, ZD9550 and ZD9556 shaker, Shanghai Anke TDL-4DB room temperature centrifuge, non-contact full-automatic ultrasonic crushing instrument of Bioruptor UCD-200 of Belgium Diagenode Company.

2.2 Experimental Method 2.2.1 Construction and Identification of NR2F1 Mutant Mice 1. At about 5 o'clock in the afternoon two days before the experiment, 0.08 ml pregnant horse serum gonadotropin was injected intraperitoneally into three-week-old C57BL/6 wild-type female mouse.

2. At about 5 o'clock in the afternoon on the day of the experiment, 0.08 ml of human chorionic gonadotropin was injected intraperitoneally into the above-mentioned C57BL/6 wild-type female mouse and they were caged with three-week-old C57BL/6 wild-type male mouse for mating.

3. On the morning of the second day after the experiment, the female mice were tested for embolus, and the female mice with embolus were picked out for later use.

4. On the afternoon of the second day after the experiment, the female mice with embolus were killed by cervical dislocation, and their fertilized eggs were taken for later use.

5. The mixed Cas9 mRNA, sgRNA and donor oligos were diluted with injection buffer (10 mm Tris HCl, pH 7.4, 0.25 mm EDTA) at concentrations of 50, 50 and 100 ng/UL, respectively.

6. The above-mentioned liquid was injected into the fertilized egg by cytoplasmic injector.

7. The injected fertilized eggs were cultured in a carbon dioxide incubator until noon the next day under 37° C. and 5% $CO_2$;

8. Embryos were transferred into the fallopian tubes of 0.5 dpc pseudopregnant ICR recipients with glass needles.

9. Take about P10 mouse, cut the tail tip tissues, extract DNA, and identify its genotypes with PCR.

2.2.2 Mouse Behavior Experiment:

2.2.2.1 Elevated-Plus Maze Experiment

The related anxiety state of mice were investigated by using the characteristics that mice like to explore in the new environment and the contradictory behavior of fear of heights with open arms at heights. In order to increase the total number of mice entering the arm and avoid hiding in the closed arm, the animals were usually placed in an open environment for 5 minutes and then placed in the maze. Similarly, the mice were placed in a room with an elevated experimental device to adapt to the environment one hour before the start of the experiment, with the red light turned on, and the room temperature was kept at 25° C. At the beginning of the experiment, hold the mouse into the palm of the hand, place it in the middle of the cross facing the closed arm, and quickly leave this room. Then another person started recording and tracking the activity movement of the mouse in another room. In the process, the times of the experimental mouse entering the open arm and the closed arm was counted, and the time of staying in the open arm and the closed arm was counted respectively; after the whole process was recorded for 5 minutes for the experiment, the mice were gently stroked, and put back into the cage. The elevated-plus table was cleaned with 70% alcohol for the experiment of the next mouse.

2.2.2.2 Three-Box Experiment a. Experimenter A entered the behavior room one hour before the experiment, took out a cage (four) of the experimental mice placed in the next room and placed them in the behavior room 1 hour. Meanwhile, the two mice needed in the experiment (note that the mice used here and the experimental mice cannot be in the same nest, and the sex should be the same) were placed in the behavior room 1 hour. Turn on the light to adapt it to the environment;

b. Experimenter A started to clean the three boxes of equipment used in the experiment about half an hour before the experiment, sprayed the 30% alcohol on all parts of the three boxes, wiped gently with a white cloth, and then wiped dry with a new clean white cloth. Then two cages and two objects were washed. And the cloth used to block personnel and the experimental area was put up.

c. At the same time, experimenter B began to debug the computer operating software: open the three-box experimental program and confirm whether the positions of the three boxes coincide with the position divided by the software. If not, please assist experimenter A in adjusting. Set the number of experimental animal and the experimental method. The specific operation is to click "Experiment" at the top left of the program, select "Animal" to start setting the experimenter, experiment content, experimental time, experiment object and number; select "Method" to start setting the experimental duration and whether to delay or not (usually two experimenters conduct the experiment without delay). At the same time, it is necessary to conduct a pre-experiment to make sure the recording equipment is normal and whether the experimental data will be stored.

d. After everything was ready, in the first round of the experiment, experimenter A put identical objects in areas 2 and 3, such as bottle caps. Close the channel between 1 and 2, 1 and 3. Gently grasp the tail of the first experimental mouse and put it on the arm sleeve of experimenter A for about 1 min to get familiar with the smell of experimenter A. The mice were then placed gently in area 1 to familiarize themselves with the experimental environment, and the step lasted 5 min.

e. 5 min later, the experiment was ready to start. Each hand of experimenter A was responsible for the channels between one side. At the same time, experimenter B clicked to prepare the experiment and canceled "automatic start". After clicking "prepare the experiment", experimenter A cooperated with B. When the channels on both sides opened, experimenter B immediately clicked on "start the experiment" (but wait until experimenter a's hand leaves the camera area). The experiment lasted 10 min, and the software recorded the time and distance of mice in each area. At this time, experimenter A returned to the personnel activity area and then gently pulled up the curtain.

f. 10 min later, the software automatically stopped the experiment. At this time, experimenter A gently guided the mice to area 1 and closed the channels on both sides.

Gently lift the mouse, put it on the arm sleeve and transfer it to an empty cage prepared in advance for use.

g. Experimenter A cleaned the experimental equipment, sprayed 30% alcohol on all parts of the three boxes, and then wiped it gently with a white cloth, and then wiped it dry with a new clean white cloth.

h. After cleaning, replace the object in area 2 with a mouse, and area 3 remain unchanged. Start the second round, gently transfer the experimental mouse to area 1, and the steps are the same as the first round. The duration was 10 min.

i. After the second round, the treatment method was the same as step 6 and the equipment was cleaned as step 7. After the cleaning was completed, the mice in area 2 remained, and the object in area 3 was replaced with another mouse. Start the third round, gently transfer the experimental mouse to area 1, and the steps were the same as the first round. The duration was 10 min.

j. After the third round, the whole experiment of an experimental mouse was completed. The mouse was put back into the cage, the equipment was cleaned, and the next experiment was started. The time required for each mouse experiment was about 50 min.

2.2.2.3 Self-Grooming Experiment

The experimental mice were placed in a feeding cage with the bottom covered with feed and the height was no more than 1 cm. The time of grooming behavior in mice in 10 minutes was recorded. The grooming position includes face, head, neck, ears, etc.

2.2.2.4 Y-Maze Experiment

The experimental mice were placed in the Y-maze, and the times and order of entering the three arms of the Y-maze within 8 minutes were recorded. Entering into 3 different arms in succession is considered as one effective arm entry. Effective arm entry rate=effective arm entry times/(total arm entry times−2)%.

2.2.3 Acquisition of Mouse Brain Tissue and Staining of Brain Slices (1) Acquisition and Fixation of Mouse Brain Tissue a. One needle tube was filled with 1×PBS, and the other needle tube was filled with 4% PFA fixing solution (4° C.), which were put aside for later use.

b. Mice were anesthetized by injecting about 180-200 μl of 4% chloral hydrate. After the mice did not move, the mice were immediately laid with their back down and abdomen up. The limbs were fixed on the white foam plate with nails. The thoracic cavity was carefully dissected to prevent excessive bleeding, the ribs were cut carefully and quickly, and the diaphragm was clipped to expose the heart.

c. Carefully pierce the needle with 1×PBS into the left ventricle and dissect the right ventricle to drain fluid. Slowly but continuously infuse 1×PBS into the heart (as shown in FIG. 3, the perfusion was normal, and blood-rich organs such as liver, spleen and kidney turn off-white).

d. When most blood has flowed out, the needle tube with 1×PBS was removed, the needle tube with 4% PFA fixative was inserted into the same needle position of left ventricle, and the mice were slowly perfused with 20 ml of fixative.

e. After perfusion, peel off the skull along the midline of the skull with surgical scissors to expose the brain, then insert the brain in the brainstem with tweezers, carefully remove the brain tissue completely, put it into in a fixative solution containing 4% PFA in a marked 15 ml corning tube overnight at 4° C.

f. Discard 4% PFA the next day, wash the brain tissue twice with PBS, replace it with 20% sucrose solution, and put it in a refrigerator at 4° C. When the mouse brain tissue sinks to the bottom, it can be used for sectioning and staining experiments.

(2) Sectioning of Mouse Brain Tissue a. Take out the mouse brain tissue from the sucrose solution, suck up the sucrose solution on the surface with absorbent paper, remove the olfactory bulb and cerebellum with a blade, leaving only the complete brain part, and the resection site should be flat, so that the mouse brain tissue can stand vertically on the ice-cutting base.

b. Apply some OTC embedding agent on the ice-cutting base, then stand the mouse brain tissue vertically on it and place it in a refrigerator at –80° C. After about 30 min, the mouse brain tissue has been frozen and firmly on the base, and can be used for ice cutting.

c. Place the frozen mouse brain tissue on the ice cutting machine back upward and ventral downward, adjust the ice cutting machine, slice thickness is about 15 mm, remove most of the brain tissue near the olfactory bulb, and collect the brain slices when the hippocampus begins to appear. Keep the brain slices flat when collecting. When the hippocampus begins to bend downward, the ice cutting can be ended. Collect all brain slices and store them in a refrigerator at –20° C.

(3) Brain Slice Staining a. Take out the slices from the refrigerator and leave them at room temperature for 10 min to dry the moisture on the slices.

b. Soak the slices in 1×PBS for 10 min, dissolve in 1×PBS, and then wash twice for 5 min each time.

c. Soak brain slices with 70% formic acid (7 ml formic acid+3 ml H₂O) for 20 min.

d. Wash the brain slice with 1×PBS 3 times for 5 min each time.

e. Cover the brain slices with 100 μl of 1×PBS containing 0.3% Triton X-100 for 20 min.

f. Drop 100 μl of sealing solution containing 0.3% Triton X-100, 0.5% NGS and 5% BSA evenly on the glass slide, and cover the glass slide with parafilm to make the sealing solution evenly distributed and sealed at room temperature for 1 hr. In the next incubation process of primary and secondary antibodies, it is also covered with parafilm.

g. Add 100 μl primary antibody (in the sealing solution according to appropriate proportion), place it in a wet box, and act at room temperature for 3 h or 4° C. overnight. PBS was used to wash 3 times, 10 min each time.

h. Add 100 μl fluorescent secondary antibody, place it in a wet box and keep it away from light for 2 hours at room temperature. PBS was used to wash 3 times, 10 min each time.

i. Add 100 μl DAPI (1:3000, diluted with deionized water), at room temperature for 2-5 min, PBS wash twice, 5 min each time.

j. Seal the cover glass with the sealing agent mowoil to avoid bubbles. After drying in the dark at room temperature, observe it under the fluorescent microscope. The prepared slides were kept away from light at 4° C.

2.2.4 Reverse transcription PCR (1) Extraction of Total Cell RNA (Refer to the Method Provided by Trizol (Invitrogen))

a. The cell sample was sucked out of culture solution, washed once with PBS, added with 1 ml Trizol after suction, and then left at room temperature for 10 min.

Transfer to a 1.5 ml RNase-free centrifuge tube, mix evenly with Vortex, add 200 μl RNase-free chloroform and mix evenly, and then leave at room temperature for 5 min.

b. 12,000 g, centrifugate at 4° C. for 15 min. Absorb supernatant (about 400 μl), add equal volume of isopropanol, and leave at room temperature for 10 min.

c. 12,000 g, centrifugate at 4° C. for 10 min. Discard the supernatant, add 1 ml of 80% ethanol-DEPC wash salt (it can be frozen at –80° C. for long-term storage).

d. 7500 g, centrifugate at 4° C. for 5 min, discard the supernatant and dry until there is no smell of alcohol.

e. Add 20-40 μl of nuclease-free (NF) water to dissolve RNA, take 2 μl and dilute 100-fold, and quantify it by OD260/280.

(2) Reverse Transcription of RNA and Amplification (RT-PCR) (Refer to the Method Provided by SuperScript RTIII (Invitrogen))

a. Take out 5 μg RNA, add 1 μl random primer (Takara), and add NF water to supplement to 12 μl. Denature at 65° C. for 5 min, and then ice bath for 5 min.

b. Add 4 μl 5*first strand buffer, 2 μl DTT, 1 μl, 10 mM dNTP, 1 μl SuperScriptIII RNase H reverse transcriptase (Invitrogen) and react according to the following procedure: 25° C., 10 min; 50° C., 60 min; 70° C., 10 min.

c. Dilute RT product to 200 μl after reaction, and store it at –20° C. after aliquoting for later use. The expression of housekeeping gene GAPDH was investigated by PCR to verify the effect of RT.

2.2.5 Quantitative PCR Reaction (Q-PCR)

Reaction system (20 μl):

2× Taq Mixture: 10 μl; Evagreen: 0.5 μl; 20 μM primer (5'+3'): 1 μl; cDNA template: 2 μl; double distilled water: 6.5 μl.

Reaction Conditions:

| 95° C. | 5 min | |
| 95° C. | 15 sec | |
| 60° C. | 15 sec | 40 cycles |

-continued

| 72° C. | 20 sec |
| 95° C. | 15 sec |
| 65° C. | 15 sec |
| 65° C.-95° C. | 30 min |
| 95° C. | 15 sec |

Quantitative PCR Results Analysis Method

The relative quantification based on the reference gene is adopted, i.e. 2-ΔΔCT method, the CT values of the target gene and the reference gene of the defined experimental sample are CT(TARGET, TEST) and CT(REF, TEST) respectively, while the calibration samples are CT(TARGET, CAL) and CT(REF, CAL) respectively. The calculation steps are as followed:

For all experimental samples and calibration samples, the CT value of the target gene is normalized with the CT value of the reference gene:

$$\Delta CT(TEST)=CT(TARGET,TEST)-CT(REF,TEST)$$

$$\Delta CT(CAL)=CT(TARGET,CAL)-CT(REF,CAL)$$

The ΔCT value of the calibration sample is used to normalize the ΔCT value of the experimental sample:

$$\Delta\Delta CT=\Delta CT(TEST)-\Delta CT(CAL)$$

Calculate the expression level ratio of the target gene between the experimental sample and the calibration sample:

$$2-\Delta\Delta CT=expression\ ratio$$

Example 1

3.1 Establishment of Mouse Model Carrying NR2F1 Gene Point Mutation

In order to study the effect and mechanism of NR2F1 gene point mutation in vivo, CRISPR/Cas9 system was used to edit the gene in mice with C57BL/6 background. Two male Founder mice were obtained by directly injecting Cas9 mRNA and transcribed sgRNA into fertilized eggs. After identification, only the 109th locus (corresponding to the 112th locus of human NR2F1) was mutated (mutated from Arg to Lys), and they were all heterozygous mutations. The possible off-target sites were also sequenced, and no obvious off-target phenomenon was found. A male Founder mouse was selected, its sperm was extracted, fertilized with the eggs of wild-type female mice, and then injected back into the uterus of surrogate female mice to obtain F1 generation. The heterozygote in F1 generation was picked out for mating. The results of observation and statistics of F2 generation were as shown in FIG. 1.

A total of three batches of 71 mice were collected, and the statistical results of their genotypes were identified. $Nr2f1^{+/+}$, wild-type mice; $Nr2f1^{+/m}$, heterozygous mutant mice; $Nr2f1^{m/m}$, homozygous mutant mice.

There were 26 wild-type mice, 45 heterozygous mutant mice and 0 homozygous mutant mice. It is difficult to obtain homozygous mutant mice (m/m) on P0 days after birth, and the ratio of heterozygous mutant mice (+/m) to wild type mice(+/+) is close to 2:1, which is in accordance with Mendelian inheritance law. This implies that mice with homozygous mutations are difficult to survive after birth, similar to the NR2F1 gene deletion mutant mice.

Example 2

3.2 Brain Morphology Analysis of Heterozygous Mutant Mice

The brains of 2-month-old wild-type and heterozygous mutant mice were collected, and the cerebral cortex was stripped and sliced for staining. The staining results are shown in FIG. 2-3. In FIG. 2, Cux1(A) and Ctip2(B) are markers of excitatory neurons. The results of immunostaining show that the number of excitatory neurons in the cerebral cortex of heterozygous mutant mice is reduced (C). In FIG. 3, GAD1(A), PV(B) and SST(C) are markers of inhibitory neurons, and the results of immunostaining statistics show that the number of inhibitory neurons in the cerebral cortex of heterozygous mutant mice increases (D).

From the above results, it can be seen that the number of excitatory projection neurons in the superficial cortex of the brain of mutant mice decreases, while the number of inhibitory interneurons increases. Apparently, there is an imbalance in the ratio of excitatory/inhibitory neurons in the cortex of heterozygous mutant mice.

Example 3

3.3 Electrophysiological Examination of Heterozygous Mutant Mice

From Example 3, it was found that the number of excitatory neurons in the cerebral cortex of the heterozygous mutant mouse decreased and the number of inhibitory neurons increased, and then the nerve conduction activity of the excitatory and inhibitory neurons was detected. The schematic diagram and statistical results (A,B) of micro excitatory potential synaptic current (mEPSC) are shown in FIG. 4. It can be seen that the nerve conduction activity of excitatory neurons in the cerebral cortex of mutant mice is significantly lower than that of wild-type mice. The nerve conduction activity of inhibitory neurons is significantly higher than that of wild-type mice.

Example 4

3.4 Behavioral Study of Heterozygous Mutant Mice

Wild-type mice are denoted by +/+, while heterozygous mutant mice are denoted by +/m. Three-box experiment, Y-maze experiment, self-grooming experiment and elevated-plus experiment were selected to test the behavioral characteristics of mice.

The three-box experiment mainly tested the social ability of mice. The experimental instrument is three transparent boxes, the boxes are connected together with a controllable gate in the middle. In the pre-experiment, the experimental mice were placed in the middle box, and the gates of the two boxes were opened allowing the mice to move to the boxes on both sides to get familiar with the environment. The formal experiment was divided into two rounds. The first round was to put the experimental mice in the middle box, with an unfamiliar stationary object in one box and an unfamiliar mouse in the other box. The mice were of the same sex, similar in age, and should not be in the same cage. After opening the gate, record the time spent by the experimental mice in the two boxes. Normal mice prefer to communicate with similar creature, but this preference is not found in autistic mice, as shown in FIG. 5. The time spent by the experimental mice with the same kind is proportional to their social ability. The time spent by the heterozygous mutant mice with similar mice was significantly less than that of wild-type mice, indicating that the social ability of heterozygous mutant mice was impaired.

The second round is to put the experimental mice in the middle box, and put a brand-new unfamiliar mouse in the box where the static object was originally placed. This mouse was of the same sex and age as the experimental mice, and it cannot be the same cage. Familiar mice are still placed in the box where the same kind of mice were originally placed. Although wild-type mice can communicate with familiar mice, they prefer to communicate more with unfamiliar mice; this preference has not been found in autistic mice, as shown in FIG. 6. The time spent by experimental mice with unfamiliar mice was proportional to their social ability. The time spent by heterozygous mutant mice with unfamiliar mice was significantly less than that of wild-type mice, indicating that the social ability of heterozygous mutant mice was impaired.

Then, the repetitive stereotyped behavior of mice was tested by Y-maze. The experimental instrument is a Y-shaped closed elevated rack. Put the mice into the maze and record the number and order of entering the arm. Only entering three different arms continuously can be counted as an effective score. Finally, the change rate of wild-type and heterozygous mutant mice (effective arm entry times/total arm entry times) was counted. The higher the change rate (alternation %), the less the repetitive stereotyped behavior. The experimental results showed that the change rate of heterozygous mutant mice was significantly lower than that of wild type, indicating that heterozygous mutant mice have obvious repetitive stereotyped behavior, as shown in FIG. 7.

Subsequent self-grooming experiments were conducted to detect repetitive stereotyped behaviors. The experiment found that the self-grooming behavior of mutant mice was obvious, and the cumulative statistical time was significantly more than that of wild-type mice, as shown in FIG. 8. This showed that mutant mice have obvious repetitive stereotyped behavior.

Figure 10:
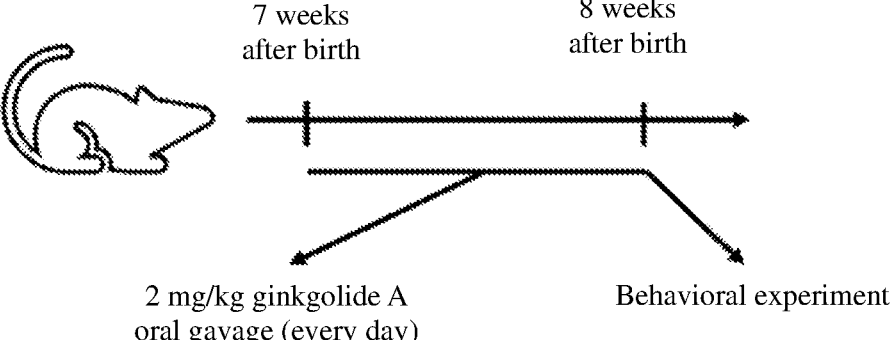
FIG. 10 shows the method of administering ginkgolide A.

The elevated-plus experiment is mainly used to detect the anxiety behavior of mice. The instrument used was a cross-shaped shelf, half open and half closed. Although normal mice liked a closed environment, curiosity drives them to explore the open space, while anxious mice preferred to stay in a closed and safe environment. The experiment results showed that heterozygous mutant mice stayed in the closed arm much longer than wild-type mice, while wild-type mice stayed in the open arm longer than heterozygous mutant mice, as shown in FIG. 10. This showed that heterozygous mutant mice were more anxious, tended to stay in a closed and safe environment, and did not like to explore new environments.

Example 5

Activity Experiment of Ginkgolide A

Ginkgolide A was administered to heterozygous mutant mice. The detailed administration scheme was as follows: the administration method was gavage treatment, the concentration of ginkgolide A was 2 mg/kg, the administration time is 7-8 weeks after the birth of mutant mice, and the administration frequency was once a day. The behavior of mutant mice was detected at 8 weeks after birth, as shown in FIG. 10.

Firstly, the three-box experiment found that the time of interaction between mutant mice fed with ginkgolide A and similar mice or unfamiliar mice was significantly increased, as shown in FIG. 11, which showed that the social defects of mutant mice were effectively alleviated.

Secondly, through the self-grooming experiment, it was found that the self-grooming time of point mutant mice fed with ginkgolide A was significantly reduced, as shown in FIG. 12, indicating that the repetitive stereotyped behavior of mutant mice was effectively alleviated.

Finally, through the elevated-plus experiment, it was found that the time for mutant mice fed with ginkgolide A to explore the open arm increased significantly, as shown in FIG. 13, indicating that the anxiety behavior of mutant mice was effectively alleviated.

To sum up, ginkgolide A can obviously relieve the social behavior disorder, repetitive stereotyped behavior and anxiety and other autistic behavior defects in mutant mice, and has a significant therapeutic effect on autism spectrum disorder, which can be used as a drug for autism spectrum disorder.

Discussion

Autism spectrum disorder is also known as autistic disorder. Patients often have great defects in perception and behavior. Obvious phenotypes of autism spectrum disorder symptoms can be observed within half a year after birth and will accompany the patients for life. Autism spectrum disorder is a chronic disease and cannot be cured. Long-term administration is often required. The goal of drug treatment is to improve the patient's self-care ability and quality of life, so drugs for treating autism spectrum disorder cannot tolerate serious side effects.

Ginkgolide A is a natural terpenoid compound extracted from *Ginkgo biloba* leaves, which has a long history of medication. Its medication safety is high and it is well known by those skilled in the medical field. It is known that Ginkgolide A has anti-anxiety effects, but no research shows that it can be used to treat autism spectrum disorder. Among many behavioral experiments of the present invention, the elevated-plus experiment can also be used to detect anxiety-related behavior, it is confirmed that ginkgolide A can relieve anxiety, and the results of other behavioral experiments directly related to autism spectrum disorder, such as the three-box experiment, the Y-maze and the self-grooming experiment, further prove that ginkgolide A does have a therapeutic effect on autistic behavior defects (such as: social behavior disorder, repetitive stereotyped behavior, etc.), indicating that ginkgolide A can treat autism spectrum disorder.

And the present invention found that the administration concentration of ginkgolide A in the treatment of autistic mice is as low as 2 mg/kg under the once-a-day administration frequency, indicating that the effective dose of ginkgolide A for the treatment of autism spectrum disorder is small, the safety is high, and it is very suitable as a common drug for the treatment of autism spectrum disorder.

All documents mentioned herein are incorporated by reference in the present invention as if each document was individually incorporated by reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A method of treating autism spectrum disorder comprising the step of:

administering to a subject having autism spectrum disorder a pharmaceutical composition consisting of (i) a therapeutically effective amount of ginkgolide A, a stereoisomer thereof, a crystal form thereof, a pharmaceutically acceptable salt thereof, a derivative thereof, or a combination thereof; and (ii) a pharmaceutically acceptable carrier, wherein the derivative of ginkgolide A is selected from the group consisting of 10-(2'-dimethylaminoethoxy)-ginkgolide A, 10-(2'-diethylaminoethoxy)-ginkgolide A, 10-((4'-methoxy-3',5'-dimethyl-2'-pyridyl)-methoxy)-ginkgolide A, and 10-( (2'-yridyl)-ethoxy)-ginkgolide A, and wherein ginkgolide A, the stereoisomer thereof, the crystal form thereof, the pharmaceutically acceptable salt thereof, the derivative thereof, or the combination thereof is present at a weight percentage greater than 50% of the pharmaceutical composition.

2. The method according to claim 1, wherein the subject is a human, a rat, or a mouse.

3. The method according to claim 1, wherein the subject carries a point mutation of an NR2F1 gene.

4. The method according to claim 1, wherein the subject carries an NR2F1-R112K point mutation.

5. The method according to claim 1, wherein ginkgolide A, the stereoisomer thereof, the crystal form thereof, the pharmaceutically acceptable salt thereof, the derivative thereof, or the combination thereof is present at a weight percentage greater than 70% of the pharmaceutical composition.

6. The method according to claim 1, wherein the dosage form of the pharmaceutical composition is selected from the group consisting of a liquid preparation and a solid preparation.

7. The method according to claim 5, wherein ginkgolide A, the stereoisomer thereof, the crystal form thereof, the pharmaceutically acceptable salt thereof, the derivative thereof, or the combination thereof is present at a weight percentage greater than 80% of the pharmaceutical composition.

8. The method according to claim 5, wherein ginkgolide A, the stereoisomer thereof, the crystal form thereof, the pharmaceutically acceptable salt thereof, the derivative thereof, or the combination thereof is present at a weight percentage greater than 90% of the pharmaceutical composition.

* * * * *